United States Patent
Yuan et al.

(10) Patent No.: US 12,327,350 B2
(45) Date of Patent: Jun. 10, 2025

(54) METHOD AND SYSTEM FOR PERFORMING VESSEL SEGMENTATION IN A MEDICAL IMAGE

(71) Applicant: Shenzhen Keya Medical Technology Corporation, Shenzhen (CN)

(72) Inventors: Shaofeng Yuan, Shenzhen (CN); Xiaomeng Huang, Shenzhen (CN); Tong Zheng, Shenzhen (CN); Yuwei Li, Bellevue, WA (US); Kunlin Cao, Kenmore, WA (US); Liwei Wang, Beijing (CN)

(73) Assignee: SHENZHEN KEYA MEDICAL TECHNOLOGY CORPORATION, Shenzhen (CN)

( * ) Notice: Subject to any disclaimer, the term of this patent is extended or adjusted under 35 U.S.C. 154(b) by 548 days.

(21) Appl. No.: 17/741,654

(22) Filed: May 11, 2022

(65) Prior Publication Data
US 2023/0177677 A1    Jun. 8, 2023

(30) Foreign Application Priority Data
Dec. 8, 2021 (CN) .......................... 202111487795.X

(51) Int. Cl.
*G06T 7/00* (2017.01)
*G06T 7/11* (2017.01)
(Continued)

(52) U.S. Cl.
CPC .............. *G06T 7/0012* (2013.01); *G06T 7/11* (2017.01); *G06T 7/60* (2013.01); *G16H 30/40* (2018.01);
(Continued)

(58) Field of Classification Search
CPC . G06T 7/0012; G06T 7/11; G06T 7/60; G06T 2200/04; G06T 2207/10012;
(Continued)

(56) References Cited

FOREIGN PATENT DOCUMENTS

| CN | 111862033 A | * | 10/2020 | ............ G06N 3/045 |
| CN | 112001925 A | * | 11/2020 | ........... G06N 3/0454 |

(Continued)

OTHER PUBLICATIONS

Fu et al., "Rapid vessel segmentation and reconstruction of head and neck angiograms using 3D convolutional neural network", 2020, Nature Communications. (Year: 2020).*
(Continued)

*Primary Examiner* — Molly Wilburn
*Assistant Examiner* — Emma N. Luke
(74) *Attorney, Agent, or Firm* — Bayes PLLC

(57) ABSTRACT

The present disclosure relates to a method, a device and a medium for performing vessel segmentation in a medical image. The method may comprise acquiring a medical image for vessel segmentation containing multiple parts, each of which contains vessels with different structural attributes. The method may comprise dividing the medical image into sub-medical images according to the parts by using a processor. The method may comprise determining individual vessel segmentation result for each part by means of using the vessel segmentation model corresponding to the part based on the sub-medical image of the part by using the processor. The method may comprise obtaining a vessel segmentation result of the medical image by means of fusing the individual vessel segmentation results of the sub-medical images of the parts by the processor. By applying the method and the device, vessel segmentation models are adapted differentially for the individual parts so as to segment the
(Continued)

vessels of the individual parts respectively, so that the entire vessel segmentation process is fast, effective, and accurate.

20 Claims, 10 Drawing Sheets

(51) Int. Cl.
  *G06T 7/60* (2017.01)
  *G16H 30/40* (2018.01)
  *G16H 40/63* (2018.01)

(52) U.S. Cl.
  CPC ......... *G16H 40/63* (2018.01); *G06T 2200/04* (2013.01); *G06T 2207/10012* (2013.01); *G06T 2207/10072* (2013.01); *G06T 2207/20021* (2013.01); *G06T 2207/20081* (2013.01); *G06T 2207/20084* (2013.01); *G06T 2207/20132* (2013.01); *G06T 2207/30008* (2013.01); *G06T 2207/30061* (2013.01); *G06T 2207/30101* (2013.01)

(58) Field of Classification Search
  CPC . G06T 2207/10072; G06T 2207/20021; G06T 2207/20081; G06T 2207/20084; G06T 2207/20132; G06T 2207/30008; G06T 2207/30061; G06T 2207/30101; G16H 30/40; G16H 40/63; G06F 18/214; G06N 3/045
  See application file for complete search history.

(56) References Cited

FOREIGN PATENT DOCUMENTS

| CN | 109919935 B | * | 2/2021 | ............... G06T 7/00 |
| CN | 113223013 A | * | 8/2021 | ............... G06T 7/11 |

OTHER PUBLICATIONS

Livne et al., "A U-Net Deep Learning Framework for High Performance Vessel Segmentation in Patients With Cerebrovascular Disease", 2019, Frontiers in Neuroscience. (Year: 2019).*

Yan: "A Three-Stage Deep Learning Model for Accurate Retinal Vessel Segmentation", 2019, IEEE Journal of Biomedical and Health Informatics. (Year: 2019).*

Zhu et al., "A 3D Coarse-to-Fine Framework for Volumetric Medical Image Segmentation", 2018, 2018 International Conference on 3D Vision. (Year: 2018).*

Yang et al., "An automated method for accurate vessel segmentation", Physics in Medicine & Biology 62 3757, 2017. (Year: 2017).*

Hu et al., "Accurate Vessel Segmentation with Optimal Combination of Features", 7th International Conference on Biomedical Engineering and Informatics, 2014. (Year: 2014).*

* cited by examiner

METHOD AND SYSTEM FOR PERFORMING VESSEL SEGMENTATION IN A MEDICAL IMAGE

CROSS-REFERENCE TO RELATED APPLICATIONS

The application is based upon and claims the benefit of priority to Chinese Patent Application No. 202111487795.X, filed Dec. 8, 2021, the entire content of which is incorporated herein by reference.

TECHNICAL FIELD

The present application relates to the technical field of medical image processing, and more specifically to a method and device for performing vessel segmentation in a medical image.

BACKGROUND

With the development of medical image equipment, doctors can use a medical image for disease screening and diagnosis, surgical planning and prognosis evaluation, etc. For example, Computed Tomography Angiography (CTA) or Magnetic Resonance Angiography (MRA) can be used to image a vessel, the vessel variation, and the vessel lesions in all parts of the body. Medical vascular image analysis plays an important role in the clinical field, and vascular image segmentation is an extremely important part in the vascular image analysis. The conventional vessel segmentation methods mainly perform a feature selection and image analysis on the angiography image to obtain a vessel segmentation result. However, this is susceptible to the surrounding structures interfering with the vessel, such as bones, plaques and supports.

Some recent vessel segmentation methods use a deep neural network to directly perform image segmentation in the angiographic image to obtain a vessel segmentation result. Although the vessel segmentation methods based on the deep neural network has significant benefits, they generally use a single model. Due to the complexity of the vascular image, the segmentation result yielded by such methods may still be suboptimal. For example, there may be an under-segmentation problem where a vessel with a larger radius and a vessel with a smaller radius are easy to be missed, and thus the vessel interruption may occur. On the other hand, there may be an over-segmentation problem that the segmentation identifies a non-vessel region in the image as including the vessel, and thus vessel adhesion noise occurs.

SUMMARY

The present disclosure is directed to solve the above technical problems. The present disclosure is intended to provide a computer-implemented method and device that can efficiently and accurately segment vessels with different structural attributes, by using a learning network, in a medical image that may contain multiple parts having structural complex and variable attributes (such as but not limited to larger vessel size range, variable vascular morphology, etc.). In the disclosed method and device, the medical image is divided into sub-medical images of the individual parts according to the differences of structural attributes of contained vessels. Appropriate learning networks are then applied to the sub-medical images of the individual parts respectively to achieve the segmentation of respective vessels. The vessel segmentation results of the individual parts are then fused to obtain the vessel segmentation result of the entire medical image. Further, the disclosed method and device can targetedly cut the vessel at special locations (such as the interface or boundary of the parts of the vessel) and perform accurate segmentations of the vessel, with respect to the different morphologies, curvatures, radii of the vessel at special locations or a part of interest preset by doctors.

In one aspect, the present disclosure relates to a method for performing vessel segmentation in a medical image. The method may include receiving a medical image containing multiple parts, which respectively contain vessels with different structural attributes. The method may further include dividing, by a processor, the medical image into sub-medical images according to the parts. The medical image is a 3D medical image and each sub-medical image is identified as a slice of interest at an adjoining portion of adjacent parts in the 3D medical image by using a slice classification model. The method may further include determining, by the processor, a vessel segmentation result for each part by applying a vessel segmentation model corresponding to the part based on the sub-medical image of the part. The method may further include obtaining, by the processor, a vessel segmentation result of the medical image fusing the individual vessel segmentation results of the sub-medical images of the parts.

In another aspect, the present disclosure relates to a device for performing vessel segmentation in a medical image. The device may include an interface and a processor. The interface may be configured to receive a medical image for vessel segmentation containing multiple parts, which respectively contain vessels with different structural attributes. The processor may be configured to divide the medical image into sub-medical images according to the parts. The processor may further be configured to determine a vessel segmentation result for each part by applying a vessel segmentation model corresponding to the part to the sub-medical image of the part. Furthermore, the processor may be configured to obtain a vessel segmentation result of the medical image of fusing the individual vessel segmentation results of the sub-medical images of the parts.

In yet another aspect, the present disclosure relates to a non-transitory computer readable medium having instructions stored thereon, and the instructions, when executed by a processor, implement the method for performing vessel segmentation in a medical image. The method may include receiving a medical image for vessel segmentation containing multiple parts, which respectively contain vessels with different structural attributes. The method may further include dividing the medical image into sub-medical images according to the parts. The method may further include determining a vessel segmentation result for each part by applying a vessel segmentation model corresponding to the part to the sub-medical image of the part. The method may further include obtaining a vessel segmentation result of the medical image by fusing the individual vessel segmentation results of the sub-medical images of the parts.

Compared with existing technologies, the embodiments of the present disclosure have the following advantages:

1. Compared with the traditional vessel segmentation method, the disclosed method adopts a deep neural network to achieve the automatic segmentation of the vessels in medical images. The disclose method can achieve: 1) a better and more accurate vessel segmentation, which is suitable for the data from different patients and also from different vendors; 2) a higher speed of vessel segmentation.

2. Compared with the current vessel segmentation method, the disclosed method also adopts a deep neural network to perform the automatic segmentation of the vessels in medical images. However, the disclosed method does not adopt a single model to complete the automatic segmentation of the vessels. Instead, to address the large variations in the morphology of vessels in the individual parts of the medical image, the medical image is firstly divided into several partial regions by a learning network, and then these partial regions are separately segmented by several corresponding learning networks respectively, and finally, the vessel segmentation results of the several partial regions are fused. Accordingly, the method has a better and more accurate vessel segmentation, and is suitable for the head and neck CTA medical image with the large variations in vessel morphology. The method solves the problem of poor vessel segmentation caused by adopting a single learning network model, and avoids vessel interruption and adhesion noise and the like, so as to avoid the influence of these conditions on doctors' diagnosis for cardiovascular diseases.

BRIEF DESCRIPTION OF THE DRAWINGS

In the drawings, which are not necessarily drawn to scale, like numerals may describe similar components in different views. Like numerals having letter suffixes or different letter suffixes may represent different instances of similar components. The drawings illustrate generally, by way of example, but not by way of limitation, various embodiments, and together with the description and claims, serve to explain the disclosed embodiments. The same reference sign in all of the drawings is used to refer to the same or similar portions when appropriate. Such embodiments are demonstrative and not intended to be exhaustive or exclusive embodiments of the present method, device or non-transitory computer readable medium having instructions for implementing the method stored thereon.

FIG. 3 (*b*) shows a vessel mask after segmentation of neck sub-medical images according to an embodiment of the present disclosure.

FIG. 3 (*c*) shows a vessel mask after segmentation of chest sub-medical images according to an embodiment of the present disclosure.

DETAILED DESCRIPTION

Detailed description will be made below in conjunction with the drawings and embodiments.

Figure 1:
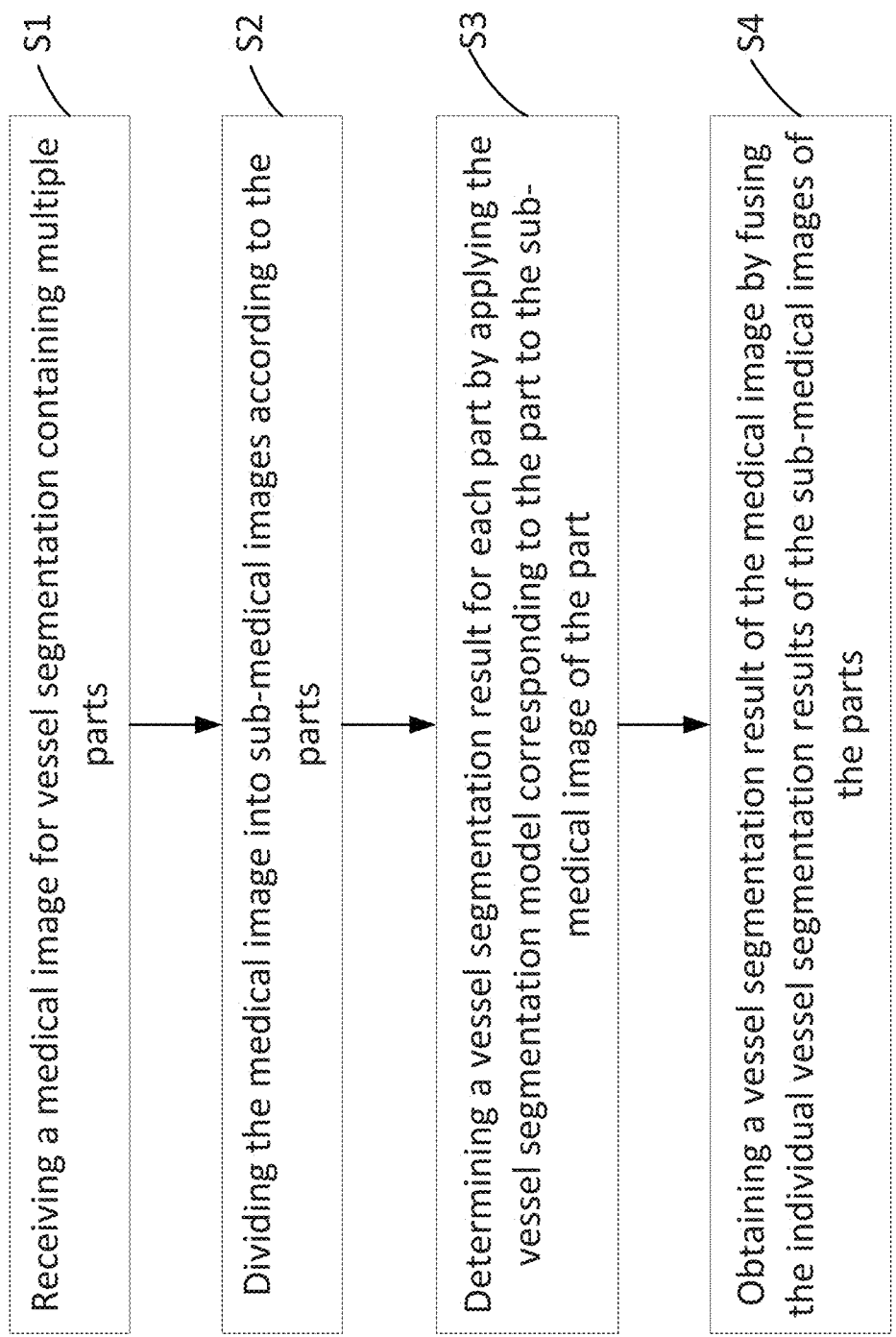
FIG. 1 shows a method for performing vessel segmentation in a medical image according to an embodiment of the present disclosure.

FIG. 1 shows a method for performing vessel segmentation in a medical image according to an embodiment of the present disclosure. As shown in FIG. 1, a method for performing vessel segmentation in a medical image begins at step S1 of acquiring a medical image for vessel segmentation containing multiple parts, each of which contains vessels with different structural attributes. In some embodiments, the structural attribute of the vessel comprises at least one of morphology and size.

At step S2, the medical image may be divided into sub-medical images of the individual parts according to the parts by using a processor. In some embodiments, the medical image is a 3D medical image, for example but not limited to a head and neck CTA image, a lung CT image and the like. For the 3D medical image, dividing the medical image into sub-medical images of the individual parts according to the parts may specifically include: identifying a slice of interest at the adjoining portion to adjacent parts in the 3D medical image based on the 3D medical image by using a slice classification model; and using the identified slices of interest to realize dividing into the sub-medical images according to the parts. In some embodiments, the slice classification model may be realized by a two-dimensional learning network and trained by training samples with the classification information of the slices of the corresponding parts.

The medical image may be the scanned image of one or more parts of the patient, and the medical image generally contains vascular tissue. The medical image may be acquired by a computer device from a post-processing workstation or Picture Archiving and Communication Systems (PACS). In this embodiment, the computer device may acquire the medical images uploaded by a technician from department of radiology to the PACS system in real time, or acquire all the medical images from the PACS system within a period at a fixed time interval. In this embodiment, the computer device may also acquire the medical image to be segmented from Hospital Information System (HIS), Clinical Information System (CIS), Radiology Information System (RIS), Electronic Medical Record (EMR) and a related cloud storage platform of medical images.

At step S3, individual vessel segmentation result for each part may be determined by the processor by means of using the vessel segmentation model corresponding to the part based on the sub-medical image of the part. In some embodiments, the individual vessel segmentation models are trained separately by using the training samples having the classification information of the vessels of the corresponding parts. Classification information may be multivariate. Correspondingly, the classification information of the vessels of the corresponding part may include multiple labels to meet doctors' needs for more detailed classification of the parts.

At step S4, a vessel segmentation result of the medical image may be obtained by the processor by means of fusing the individual vessel segmentation results of the sub-medical images of the parts.

The present disclosure is illustrated in the following with a head and neck CTA medical image as an example. However, it should be noted that the present disclosure may be applied to various medical images that contain multiple parts. For example, the medical image may include at least one of a head and neck CTA image, a head and neck MRA image, and a lung CT image.

Figure 2:
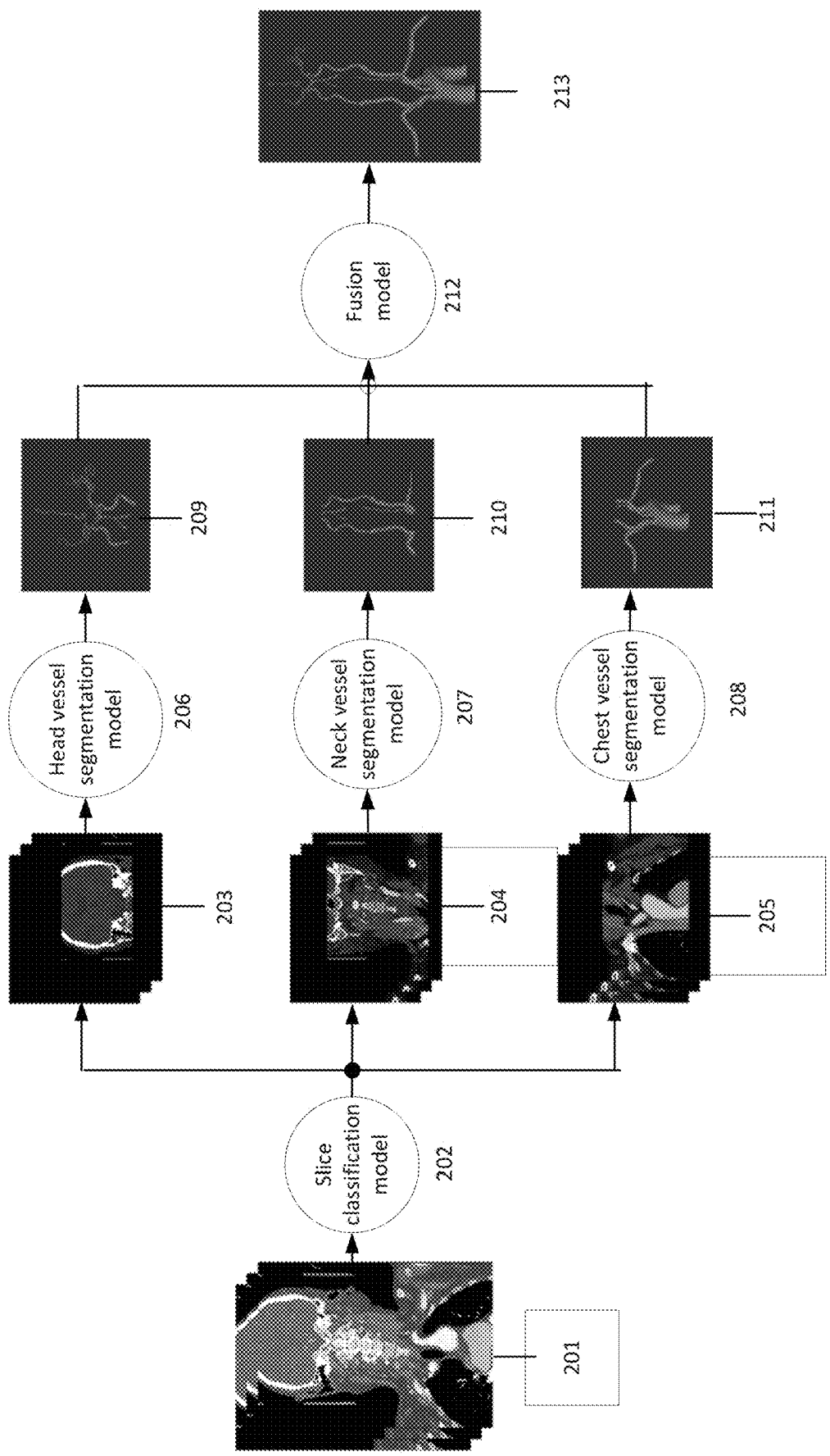
FIG. 2 shows a process for performing vessel segmentation in a medical image according to the embodiment of the present disclosure.

FIG. 2 shows a process for performing vessel segmentation in a medical image according to the embodiment of the present disclosure. As shown in FIG. 2, firstly, the head and neck CTA 3D medical image 201 is divided by a slice classification model 202 into 3 sub-regions, namely, a head region 203, a neck region 204 and a chest region 205. There are significant differences in the structural attributes of the vessels in the individual regions. For example, the artery of the head region 203 has a vessel radius R1; the artery of the neck region 204 has a vessel radius R2; and the artery of the chest region 205 has a vessel radius R3. For example, the vessel curvature of the artery of the head region 203 is significantly higher than that of the neck region 204 and that of the chest region 205. For another example, the vessel density of the artery of the head region 203 is significantly higher than that of the neck region 204 and that of the chest region 205.

A head vessel segmentation model 206 may be adopted to perform vessel segmentation for the head region 203, a neck vessel segmentation model 207 may be adopted to perform vessel segmentation for the neck region 204, and a chest vessel segmentation model 208 may be adopted to perform vessel segmentation for the chest region 205. Finally, the respective vessel segmentation results 209, 210, and 211 of the head region 203, the neck region 204 and the chest region 205 are fused by fusion model 212 as the final vessel segmentation result 213.

In some embodiments, before performing various processing on the medical image or the sub-medical image by using the processor, a standardized processing may be performed on the medical image or the sub-medical image. For example, the standardized processing may include: resampling the medical image or the sub-medical image to obtain the medical image or the sub-medical image with a corresponding voxel interval, and clipping intensity value with a predefined window width and window level and normalizing the gray value of the medical image for the resampled medical image or the sub-medical image.

In some embodiments, determining by the processor individual vessel segmentation result for each part by means of using the vessel segmentation model corresponding to the part based on the sub-medical image of the part may specifically include: performing a coarse segmentation in the sub-medical image of each part to obtain a first image patch containing a target region of the vessel to be segmented. Here, the coarse segmentation may be implemented by various means, such as a coarse segmentation for the vessel or a coarse segmentation for characteristic structures (bones or tissues) of the target region, in order to reduce the workload of subsequent further segmentation. Then, a first vessel segmentation model may be used based on the first image patch containing the target region, so as to determine a first vessel segmentation result as the vessel segmentation result of the sub-medical image of the part.

Figure 3A:
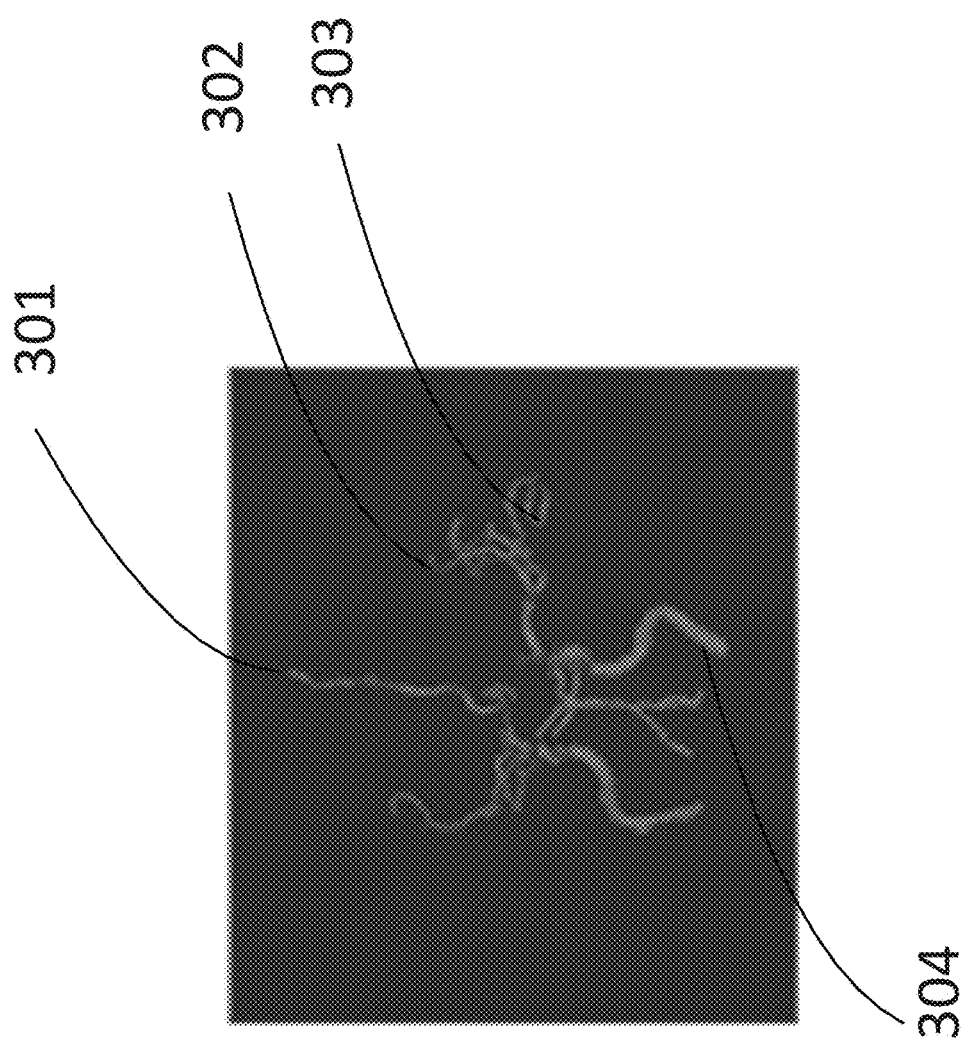
FIG. 3 (*a*) shows a vessel mask after segmentation of head sub-medical images according to an embodiment of the present disclosure.
Figure 3B:
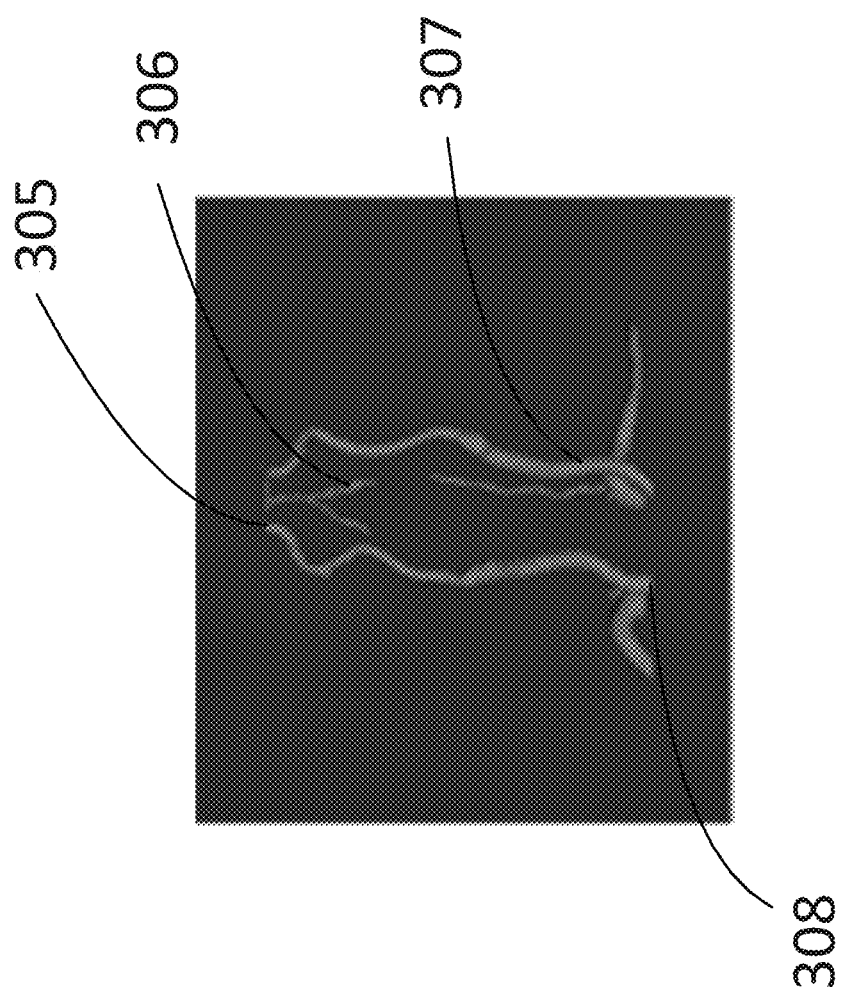
Figure 3C:
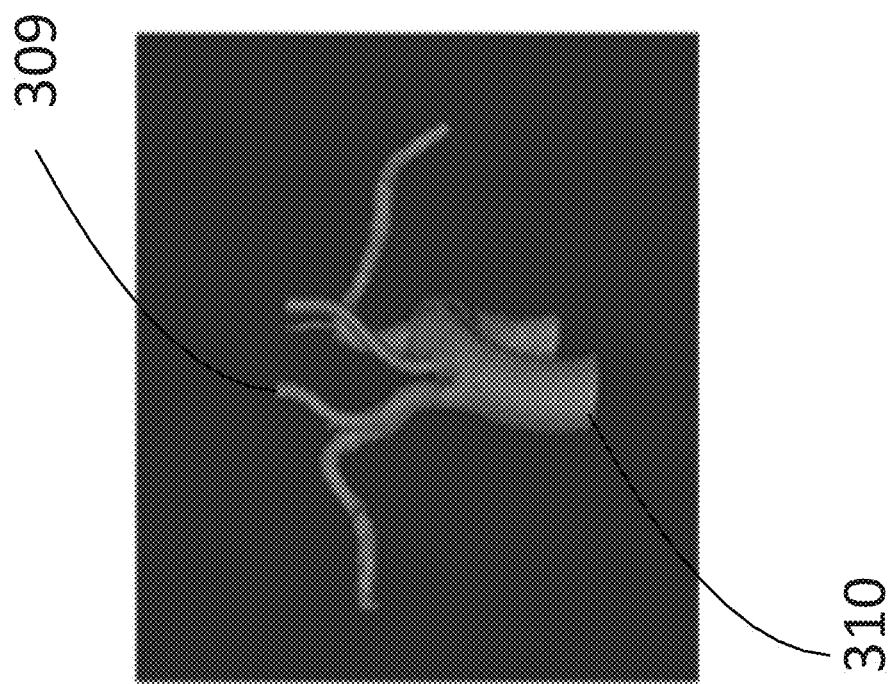

Further, the method for performing vessel segmentation in a medical image may further include, for at least one part: performing centerline extraction on the determined first vessel segmentation result, and cropping a second image patch at the end of the extracted centerline. For example, FIG. 3(a), FIG. 3(b) and FIG. 3(c) respectively show the vessels after segmentation of the head sub-medical image, the neck sub-medical image and the chest sub-medical image according to the embodiments of the present disclosure. Ends of vessel centerlines are respectively labeled as 301 and 304 in FIG. 3(a), 305 and 308 in FIG. 3(b), and 309 and 310 in FIG. 3 (c). Accordingly, the second image patch may be cropped at the ends 301 and 304 of the vessel centerline in FIG. 3(a), the ends 305 and 308 of the vessel centerline in FIG. 3(b), and the ends 309 and 310 of the vessel centerline in FIG. 3(c). Note that the "end" in this article may contain a region surrounding an endpoint, and the cropped second image patch may contain the image information on the vessel adjoining region of the head, the neck and the chest.

A second vessel segmentation model may be used based on the second image patch at the end, so as to determine a second vessel segmentation result at the end. Compared with the first vessel segmentation model, the second vessel segmentation model focuses more on a small field of view, which is beneficial to accurate segmentation of various sections of vessel with variable structural attributes at the end, so as to avoid vessel interruption, adhesion noise and so on.

Finally, the first vessel segmentation result and the second vessel segmentation result may be fused to obtain the vessel segmentation result of the sub-medical image of at least one of the parts. Benefitting from the coarse segmentation in which the target region is segmented by the first vessel segmentation model, and the fine segmentation of the edge vessel in which the image patch at the end is segmented by the second vessel segmentation model, a more accurate segmentation result for complex vessels across multiple parts may be obtained that avoids vessel interruption and adhesion noise, and meanwhile the workload is lower and the computation is faster.

In some embodiments, the at least one of the parts for which the centerline is extracted and the image patch is cropped from the end of the extracted centerline may be directly set as each part in the multiple parts, or as a part of interest preset by a doctor in the multiple parts. By presetting the part of interest, the doctor expresses the feedback of more accurate requirements and greater segmentation difficulty for the vessel segmentation result of the part of interest. Therefore, in response to the doctor's feedback and in order to meet the doctor's requirements, the following processes may be performed targetedly on the part of interest: extraction centerline of the vessel; cropping image patch in the end of centerline; and fine segmentation of vessels in a small field of view.

Further, the method for performing vessel segmentation in a medical image may further include selecting a part prone to interruption in the segmentation result of the vessel at the adjoining portion to the adjacent part from the multiple parts, as the at least one of the parts. In this way, the vessel interruption at the adjoining portion of adjacent parts may be significantly reduced or even avoided.

Further, the method for performing vessel segmentation in a medical image may further include: selecting a part where the segmented vessel at the end of the adjoining portion to the adjacent part meets at least one of the following conditions, from the multiple parts, as the at least one of the parts. By applying the processes of "extraction centerline of the vessel; cropping image patch in the end of centerline; and fine segmentation of vessel in a small field of view" only for the parts meeting these conditions, the vessel interruption at the adjoining portion of adjacent parts may be significantly reduced or even avoided, while reducing the workload and speeding up the segmentation.

These judgment conditions may include: the diameter of the vessel at the end of the adjoining portion to the adjacent part is less than a first predetermined threshold. For example, at the end 302 of FIG. 3(*a*), the end 306 and the end 307 of FIG. 3(*b*), a vessel with a diameter less than the first predetermined threshold is more prone to interruption when segmented.

These judgment conditions may include: the curvature of the vessel at the end of the adjoining portion to the adjacent part is larger than a second predetermined threshold. For example, at the end 303 of FIG. 3(*a*), a vessel with a curvature larger than the second predetermined threshold is more prone to interruption when segmented.

These judgment conditions may include: the contrast of the vessel at the end of the adjoining portion to the adjacent part to the surrounding region is less than a third predetermined threshold. For example, at the end 302 of FIG. 3(*a*) and the end 307 of FIG. 3(*b*), a vessel with a contrast to the surrounding region less than the third predetermined threshold is more prone to interruption and/or adhesion noise when segmented.

In the present disclosure, different body parts such as head, neck and chest are mainly taken as examples of the multiple parts. But it should be noted that the multiple parts may be not only different body parts, but also be at least one of different organs, and different organ parts in the same organ.

Figure 4:
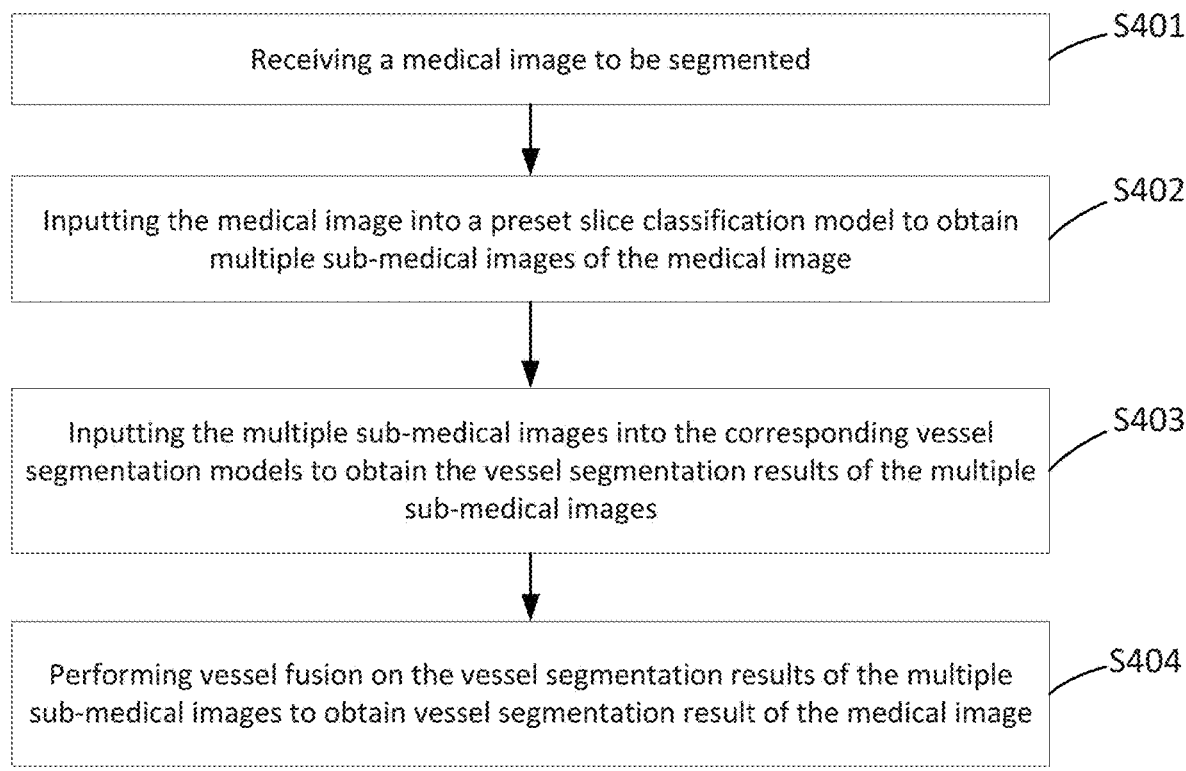
FIG. 4 shows an exemplary process for performing vessel segmentation in a medical image according to the embodiment of the present disclosure.

In combination with FIG. 4, a detailed process of the method for performing vessel segmentation in a medical image is described explanatorily below. As shown in FIG. 4, at step S401, a medical image to be segmented may be acquired.

In this embodiment, after the computer device acquires the medical image to be segmented, it may also perform preprocessing on the medical image. The preprocessing may include: converting the medical image format from Digital Imaging and Communications in Medicine (DICOM) format to NIFTI format, resampling the medical image to acquire a medical image with a first voxel interval, setting the window width and window level to shrink the gray value range of the medical image, and normalizing the maximum and minimum values of the image to [0, 1] to obtain a standardized image. Here, the resampling means to resample image given a fixed voxel interval or fixed image size. Given an original image with its original size (512, 512, 256) and the original voxel interval (0.6, 0.6, 0.4), if the target voxel interval is (1.0, 1.0, 1.0), then it can be calculated that the target size is (307, 307, 102). The specific calculation is that 512×0.6/1.0=307, and 256×0.4/1.0=102. When converting from the size (512, 512, 256) to (307, 307, 102), the gray of each voxel needs to be redetermined and obtained by the resampling. The voxel interval is a comprehensive manifestation of the pixel interval in each dimension. The voxel interval is used for the three-dimensional image, while the pixel interval is used for the two-dimensional image. The voxel interval specifically means a distance from the center of a voxel to the center of another adjacent voxel, in millimeters. For example, when the voxel interval is (0.6, 0.6, 0.4), it may be understood that the size of one voxel represents the actual size or physical size of 0.6×0.6×0.4 cubic millimeters.

At step S402, the medical image may be input into a preset slice classification model to obtain several sub-medical images of the medical image. Here, the slice classification model may be obtained by training according to training samples with information of the parts of interest.

Specifically, the computer device may input the above-mentioned preprocessed medical image into the preset slice classification model. The part determination results may be obtained by performing the feature extraction and feature classification on the medical image by the slice classification model, and the part determination results may be the results of dividing the medical image before the preprocessing into several sub-medical images. In this embodiment, the part determination results may be the results of dividing the medical image before the preprocessing into three sub-medical images, and these results respectively represent a head sub-medical image, a neck sub-medical image, and a chest sub-medical image. Obviously, two slices of interest are required to determine three sub-medical images.

Therefore, the above slice classification model is obtained by training according to training samples with slice classification information of the parts of interest. The training method of the slice classification model may include: based on two slices of interest marked by an experienced radiology doctor in the images as training samples, collecting the head, neck, and chest slices according to the marked slice of interest information as training samples and the gold standard classification information corresponding to the training samples. Then, the training samples are input into the slice classification model to obtain the slice classification result of the training samples, and the loss between the slice classification result and the gold standard classification information is calculated. Then, the network parameter of the slice classification model is adjusted according to the loss. When the loss is less than or equal to the preset threshold or reaches convergence, it indicates that the slice classification model training has converged. In this embodiment, a cross-entropy loss function or other types of loss function may be used when calculating the loss. When adjusting the network parameter, a stochastic gradient descent (SGD) optimizer or other types of optimizers may be used.

In this embodiment, since the slice classification is performed on the medical image, the slice classification model described above may be a two-dimensional model. The two-dimensional model may be a convolutional neural network model, a recurrent neural network model or other deep learning models, which is not specifically limited here. For the obtained part determination results of the medical image, see the left side of FIG. 2, that is, one medical image is divided into three sub-medical images.

At step S403, the several sub-medical images may be input into the corresponding vessel segmentation models to obtain the vessel segmentation results of the several sub-medical images. Here, the several vessel segmentation models are obtained by training according to training samples with classification information of the vessels of interest.

Specifically, the computer device may preprocess the above-mentioned several sub-medical images and input them into the preset several vessel segmentation models to obtain the vessel segmentation results of the several sub-medical images. In this embodiment, one medical image is divided into three sub-medical images, which are then input into the three preset vessel segmentation models respectively to obtain three vessel segmentation results respectively. The three vessel segmentation models are a head vessel segmentation model, a neck vessel segmentation model, and a chest vessel segmentation model respectively. The result of the above slice classification model is a head sub-medical image, a neck sub-medical image, and a chest sub-medical image.

Before the head medical image is input into the preset head vessel segmentation model, the computer device performs the preprocessing on this sub-medical image. The preprocessing may include resampling this sub-medical image to acquire a medical image with a second voxel interval, setting the window width and window level to shrink the gray value range of the medical image, and normalizing the maximum and minimum values of the image to [0, 1] to obtain a standardized image. The head vessel segmentation result may be obtained by performing a feature extraction and feature mapping on the sub-medical image by the head vessel segmentation model. The vessel segmentation result may be the result after distinguishing the head vessel region image from the background image.

Therefore, the above head vessel segmentation model is obtained by training based on training samples with information of the vessel of interest. The training method of the vessel segmentation model may include: based on the head vessel marked by an experienced radiology doctor in the images as training samples, and using the marked information as the gold standard in training. Then, the images as training samples are input into the head vessel segmentation model to obtain the head vessel segmentation result, and the loss between the head vessel segmentation result and the gold standard is calculated. The network parameter of the head vessel segmentation model is adjusted according to the loss. When the loss is less than or equal to the preset threshold or reaches convergence, it indicates that the head vessel segmentation model training has converged. In this embodiment, a Dice loss function, a cross-entropy loss function or other types of loss function may be used when calculating the loss, which is not specifically limited here. When adjusting the network parameter, a stochastic gradient descent (SGD) optimizer or other types of optimizers may be used.

Before the neck sub-medical image is input into the preset neck vessel segmentation model, the computer device performs the preprocessing on this medical image. The preprocessing may include resampling this medical image to acquire a medical image with a third voxel interval, setting the window width and window level to shrink the gray value range of the medical image, and normalizing the maximum and minimum values of the image to [0, 1] to obtain a standardized image. The neck vessel segmentation result may be obtained by performing a feature extraction and feature mapping on the medical image by the neck vessel segmentation model. The vessel segmentation result may be the result after distinguishing the neck vessel region image from the background image.

Therefore, the above neck vessel segmentation model is obtained by training based on training samples with information of the vessel of interest. The training method of the vessel segmentation model may include: based on the neck vessel marked by an experienced radiology doctor in the images as training samples, and using the marked information as the gold standard in training. Then, the images as training samples are input into the neck vessel segmentation model to obtain the neck vessel segmentation result, and the loss between the neck vessel segmentation result and the gold standard is calculated. The network parameter of the neck vessel segmentation model is adjusted according to the loss. When the loss is less than or equal to the preset threshold or reaches convergence, it indicates that the neck vessel segmentation model training has converged. A Dice loss function, a cross-entropy loss function or other types of loss function may be used when calculating the loss, which is not specifically limited here. When adjusting the network parameter, a stochastic gradient descent (SGD) optimizer or other types of optimizers may be used.

Before the chest sub-medical image is input into the preset chest vessel segmentation model, the computer device performs the preprocessing on this medical image. The preprocessing may include resampling this medical image to acquire a medical image with a fourth voxel interval, setting the window width and window level to shrink the gray value range of the medical image, and normalizing the maximum and minimum values of the image to [0, 1] to obtain a standardized image. The chest vessel segmentation result may be obtained by performing a feature extraction and feature mapping on the medical image by the chest vessel segmentation model. The vessel segmentation result may be the result after distinguishing the chest vessel region image from the background image.

Therefore, the above chest vessel segmentation model is obtained by training based on training samples with information of the vessel of interest. The training method of the vessel segmentation model may include: based on the chest vessel marked by an experienced radiology doctor in the images as training samples, and using the marked information as the gold standard in training. Then, the images as training samples are input into the chest vessel segmentation model to obtain the chest vessel segmentation result, and the loss between the chest vessel segmentation result and the gold standard is calculated. The network parameter of the chest vessel segmentation model is adjusted according to the loss. When the loss is less than or equal to the preset threshold or reaches convergence, it indicates that the chest vessel segmentation model training has converged. A Dice loss function, a cross-entropy loss function or other types of loss function may be used when calculating the loss, which is not specifically limited here. When adjusting the network parameter, a stochastic gradient descent (SGD) optimizer or other types of optimizers may be used.

In this embodiment, since vessel segmentation is performed in several sub-medical images, the above several vessel segmentation models may be three-dimensional models. The three-dimensional model may be a convolutional neural network model, a recurrent neural network model or other deep learning models, such as 3D U-Net, 3D V-Net, which is not limited in this embodiment. For the obtained multiple vessel segmentation results of multiple sub-medical images, see the middle of FIG. 2, that is, one sub-medical image corresponds to one vessel segmentation result.

In this embodiment, considering the GPU memory size of the computer device, there may be insufficient GPU memory when processing the entire sub-medical images. Therefore, the computer device may also crop image patches of the same size in the upper left corner of the medical image (such as cropped image patch with size of 180×180×180), and each image patch is input into the vessel segmentation model to obtain the vessel segmentation result of each image patch. Then, the vessel segmentation result of each image patch is merged in the cropping order into the vessel segmentation result of the entire sub-medical image.

At step S404, the vessel segmentation result of the medical image may be obtained by performing vessel fusion on the vessel segmentation results of the several sub-medical images.

Specifically, the computer device may use a linear or non-linear fusion method to perform vessel fusion of the vessel segmentation results of the several sub-medical images to obtain the final vessel segmentation result of the medical image. The obtained vessel segmentation result of the image may be seen on the right side of FIG. 2.

In the method for performing vessel segmentation in a medical image provided by the present embodiments, the computer device first input the medical image to be segmented into the preset slice classification model to obtain several sub-medical images of the medical image. Then, the several sub-medical images to be segmented are input into the preset vessel segmentation models respectively to obtain the sub vessel segmentation results of the several sub-medical images. Finally, the vessel segmentation result of the entire medical image is obtained by performing vessel fusion on the sub vessel segmentation results. The slice classification model is obtained by training according to training samples with the information of the parts of interest. The several vessel segmentation models are obtained by training according to training samples with the information of the vessel of interest. The slice classification model obtained from this training takes into account the characteristics of the head and neck sub-medical images containing different vessel sizes from bottom to top, and thus can make the entire vessel segmentation process fast and effective. The several vessel segmentation models obtained from this training take into account that vessels from different patients in the same part have similar morphology, trend, and radius, and thus can make the several vessel segmentation models more concerned with the vessel segmentation process of the corresponding part, and thus can better realize the accurate segmentation of the vessel.

Figure 5:
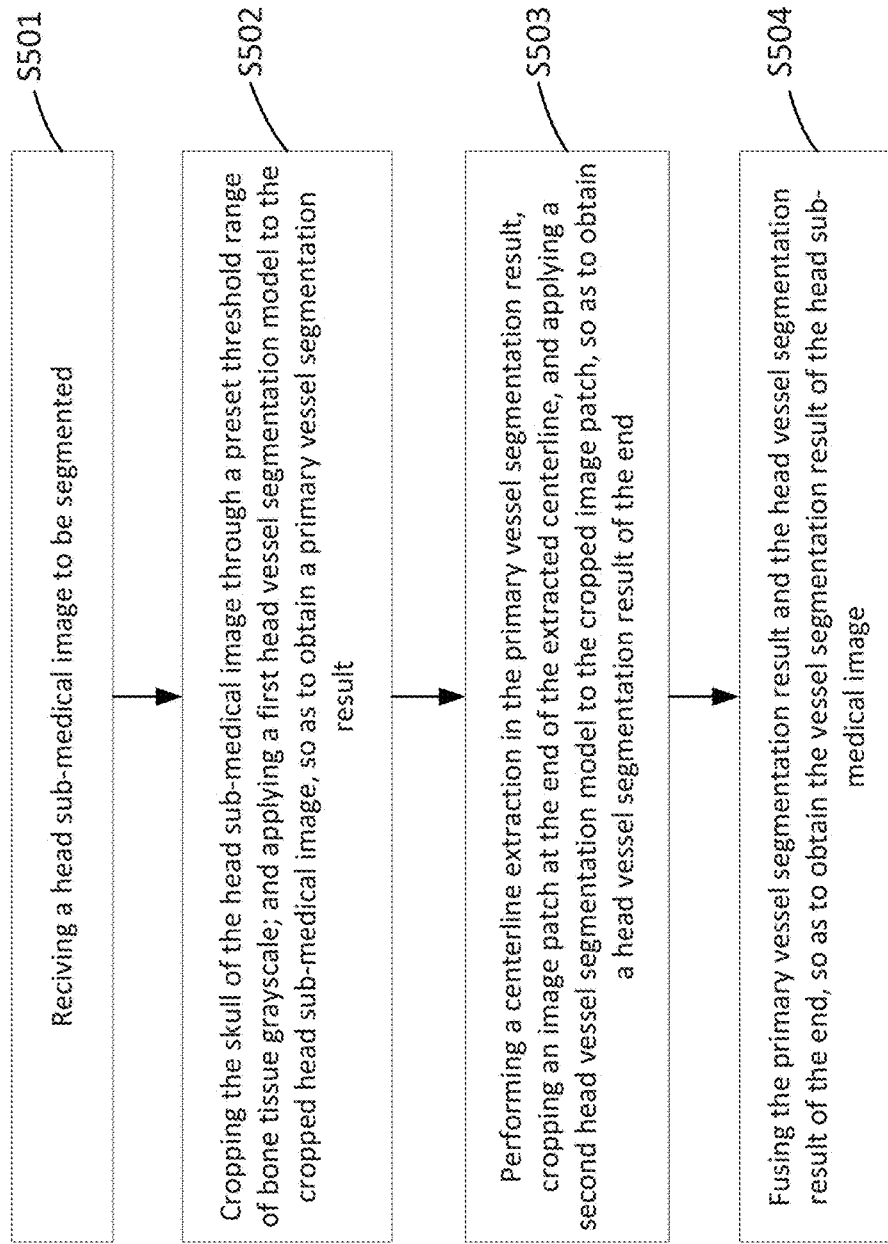
FIG. 5 shows a method for performing vessel segmentation in head sub-medical images according to the embodiment of the present disclosure.

FIG. 5 shows a method for performing vessel segmentation in a head sub-medical image according to the embodiment of the present disclosure. As shown in FIG. 5, the method of performing vessel segmentation in the head sub-medical image may include the following steps.

At step S501, a head sub-medical image to be segmented is acquired. Specifically, the head sub-medical image to be segmented is the cropped sub-medical image output by the slice classification model. The medical image generally contains vascular tissue, brain tissue, and skull tissue.

In this embodiment, the head sub-medical image to be segmented may be obtained by dividing the head CTA angiographic image according to the parts.

At step S502, the skull of the head sub-medical image may be segmented through a preset threshold range of bone tissue grayscale, and the head sub-medical image containing the skull region is cropped; and a primary vessel segmentation result is obtained by applying a first head vessel segmentation model to the copped head sub-medical image.

Specifically, before the medical image is input into a preset first head vessel segmentation model, the computer device performs the preprocessing on this medical image. The preprocessing may include resampling this medical image to acquire a medical image with a fifth voxel interval, setting the window width and window level to shrink the gray value range of the medical image, and normalizing the maximum and minimum values of the image to [0, 1] to obtain a standardized image. A first head vessel segmentation result may be obtained by performing a feature extraction and feature mapping on the medical image by the first head vessel segmentation model. This vessel segmentation result may be the result after distinguishing the head vessel region image from the background image.

Specifically, a threshold range [a, b] of a pair of bone tissues from good skull segmentation is obtained through a large amount of data verification. A gray level less than the gray level threshold a is set to be 0, a gray level greater than the gray level threshold b is set to be 0, and a gray level not less than a and not greater than b is set to be to 1, and a skull segmentation result is obtained. By calculating the skull segmentation, a bounding box [x1, y1, z1, x2, y2, z2] surrounding the skull is obtained. The head medical image is cropped by using the bounding box. This disclosure does not specifically limit the skull segmentation method.

At step S503, a centerline extraction is performed on the primary vessel segmentation result, an image patch is cropped at the end of the extracted centerline, and a head vessel segmentation result of the end is obtained by applying a second head vessel segmentation model.

Specifically, in this embodiment, said performing centerline extraction on the primary vessel segmentation result may be implemented by a three-dimensional skeletonization method, which is not limited in this embodiment. By analyzing the skeletonized result, the end position of the vessel can be obtained. The medical image is cropped at the end position of the vessel, and then input into the preset second head vessel segmentation model to obtain the vessel segmentation result at the end.

In this embodiment, before the medical image patch is input into the preset second head vessel segmentation model, the computer device performs the preprocessing on the medical image patch. The preprocessing may include resampling the medical image patch to acquire a medical image with a sixth voxel interval, setting the window width and window level to shrink the gray value range of the medical image, and normalizing the maximum and minimum values of the image to [−1, 1] to obtain a standardized image.

At step S504, the primary vessel segmentation result and the head vessel segmentation result of the end may be fused to obtain the vessel segmentation result of the head sub-medical image.

Therefore, the above first head vessel segmentation model is obtained by training based on training samples with information of the vessel of interest. The training method of the vessel segmentation model may include: based on the head vessel marked by an experienced radiology doctor in the images as training samples, and using the marked information as the gold standard in training. Then, the images as training samples are input into the head vessel segmentation model to obtain the head vessel segmentation result, and the loss between the head vessel segmentation result and the gold standard is calculated. The network parameter of the head vessel segmentation model is adjusted according to the loss. When the loss is less than or equal to the preset threshold or reaches convergence, it indicates that the head vessel segmentation model training has converged. In this embodiment, a Dice loss function, a cross-entropy loss function or other types of loss function may be used when calculating the loss, which is not specifically limited here. When adjusting the network parameter, a stochastic gradient descent (SGD) optimizer or other types of optimizers may be used.

Figure 6:
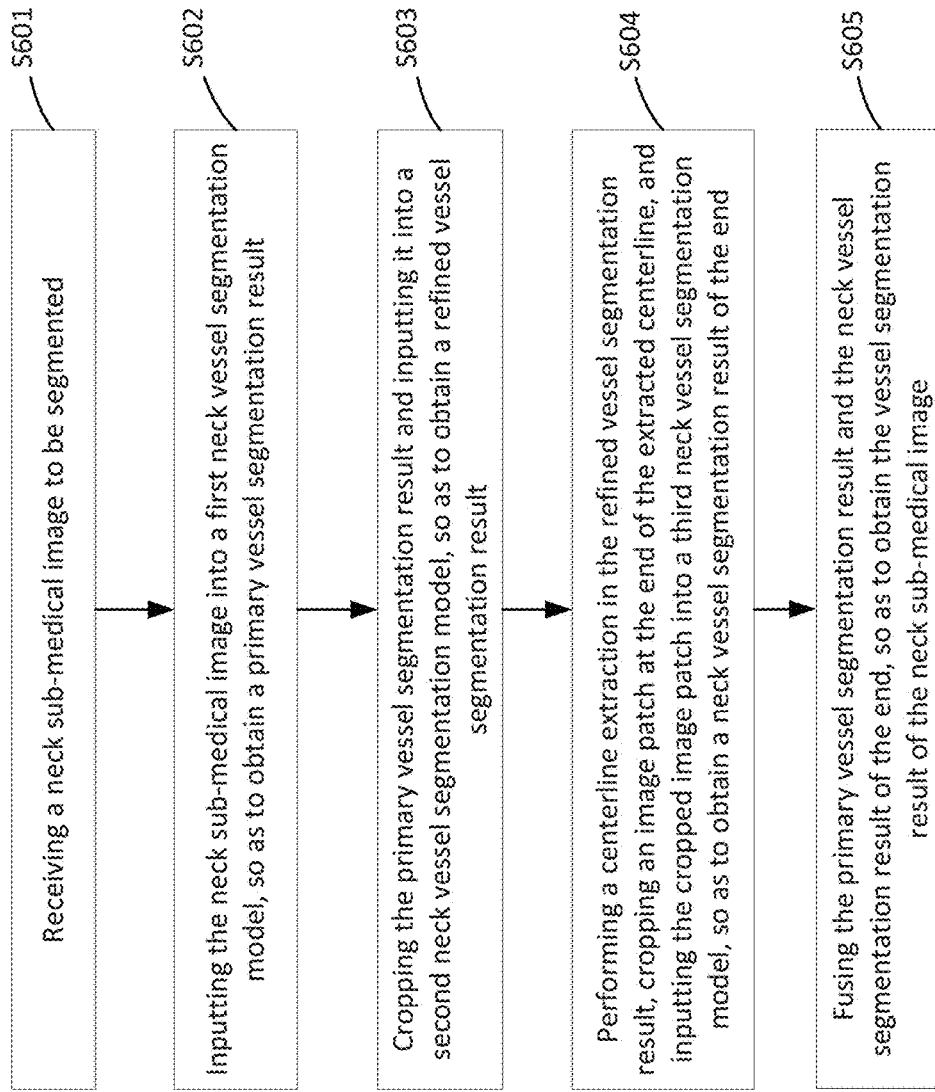
FIG. 6 shows a method for performing vessel segmentation in neck sub-medical images according to the embodiment of the present disclosure.

FIG. 6 shows a method for performing vessel segmentation in a neck sub-medical image according to the embodiment of the present disclosure. As shown in FIG. 6, the method for performing vessel segmentation in a neck sub-medical image may include, at step S601, acquiring a neck sub-medical image to be segmented. Specifically, the neck sub-medical image to be segmented may be the cropped sub-medical image output by the slice classification model, and the medical image generally contains vascular tissue and bone tissue.

In the present disclosure, the neck sub-medical image to be segmented may be derived from a neck CTA angiographic image. The present disclosure does not limit the source of the neck sub-medical image.

At step S602, the neck sub-medical image may be input into a first neck vessel segmentation model to obtain a primary vessel segmentation result.

Specifically, before the medical image is input into the preset first neck vessel segmentation model, the computer device performs the preprocessing on this medical image. The preprocessing may include resampling this medical image to acquire a medical image with a seventh voxel interval, setting the window width and window level to shrink the gray value range of the medical image, and normalizing the maximum and minimum values of the image to [−1, 1] to obtain a standardized image. A first neck vessel segmentation result may be obtained by performing a feature extraction and feature mapping on the medical image by the first neck vessel segmentation model. This vessel segmentation result may be the result after distinguishing the neck vessel region image from the background image.

In this embodiment, the neck vessel region may also exist in the form of multiple labels. For example, the left common carotid artery may be defined as label 1, the right common carotid artery as label2, the brachiocephalic trunk as label 3, the left internal carotid artery as label 4, and the right internal carotid artery as label 5, etc.

At step S603, the neck sub-medical image may be cropped by using the primary vessel segmentation result, and the cropped image is input into a second neck vessel segmentation model to obtain a refined vessel segmentation result.

Specifically, before the medical image is input into the preset second neck vessel segmentation model, the computer device performs the preprocessing on this medical image. The preprocessing may include resampling this medical image to acquire a medical image with an eighth voxel interval, setting the window width and window level to shrink the gray value range of the medical image, and normalizing the maximum and minimum values of the image to [−1, 1] to obtain a standardized image. A second neck vessel segmentation result may be obtained by performing a feature extraction and feature mapping on the medical image by the second neck vessel segmentation model. This vessel segmentation result may be the result after distinguishing the neck vessel region image from the background image.

In this embodiment, the neck vessel region may also exist in the form of multiple labels. For example, the left common carotid artery may be defined as label 1, the right common carotid artery as label 2, the brachiocephalic trunk as label 3, the left internal carotid artery as label 4, and the right internal carotid artery as label 5, etc.

At step S604, a centerline extraction is performed on the refined vessel segmentation result, an image patch is intercepted at the end of the extracted centerline, and the cropped image patch is input into a third neck vessel segmentation model to obtain a neck vessel segmentation result of the end.

Specifically, in this embodiment, said performing centerline extraction on the refined vessel segmentation result may be implemented by a three-dimensional skeletonization method, which is not limited in this embodiment. By analyzing the skeletonized result, the end position of the vessel can be obtained. The medical image is cropped at the end position of the vessel, and then input into the preset third neck vessel segmentation model to obtain the vessel segmentation result at the end.

In this embodiment, before the medical image is input into the preset third neck vessel segmentation model, the computer device performs the preprocessing on this medical image. The preprocessing may include resampling this medical image to acquire a medical image with a ninth voxel interval, setting the window width and window level to shrink the gray value range of the medical image, and normalizing the maximum and minimum values of the image to [−1, 1] to obtain a standardized image.

At step S605, the primary vessel segmentation result and the neck vessel segmentation result of the end may be fused to obtain the vessel segmentation result of the neck sub-medical image.

Figure 7:
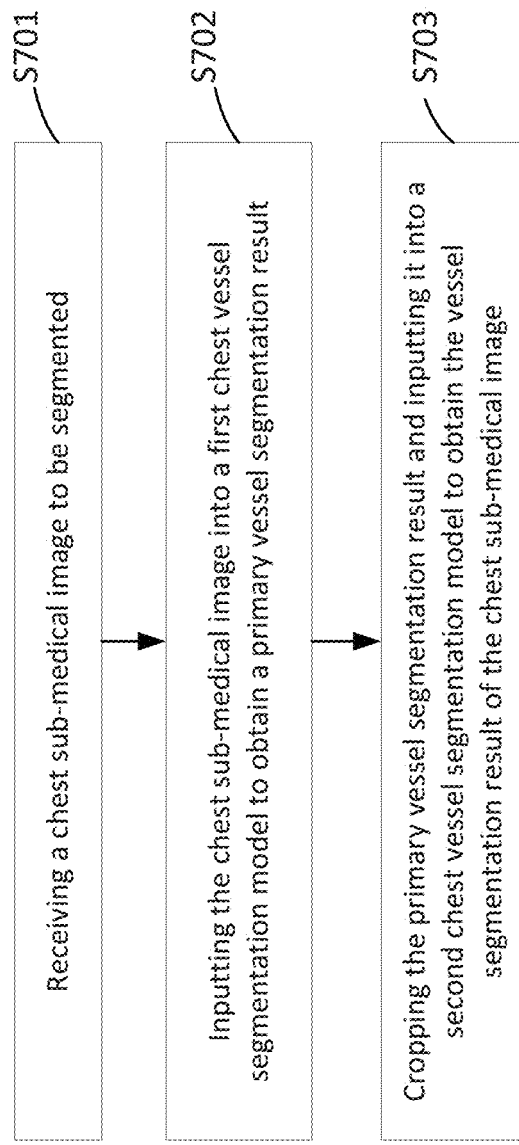
FIG. 7 shows a method for performing vessel segmentation in chest sub-medical images according to the embodiment of the present disclosure.

FIG. 7 shows a method for performing vessel segmentation in a chest sub-medical image according to the embodiment of the present disclosure. As shown in FIG. 7, the method for performing vessel segmentation in a chest sub-medical image may include, at step S701, acquiring a chest sub-medical image to be segmented. Specifically, the chest sub-medical image to be segmented may be the cropped sub-medical image output by the slice classification model, and the medical image generally contains vascular tissue, aortic arch tissue, bone tissue, lung parenchymal tissue, and the like.

In this embodiment, the chest sub-medical image to be segmented may be derived from a chest CTA angiographic image. The present disclosure does not limit the source of the chest sub-medical image.

At step S702, a chest sub-medical image may be input into a first chest vessel segmentation model to obtain a primary vessel segmentation result.

Specifically, before the medical image is input into the preset first chest vessel segmentation model, the computer device performs the preprocessing on this medical image. The preprocessing may include resampling this medical image to acquire a medical image with a tenth voxel interval, setting the window width and window level to shrink the gray value range of the medical image, and normalizing the maximum and minimum values of the image to [−1, 1] to obtain a standardized image. A first chest vessel segmentation result may be obtained by performing a feature extraction and feature mapping on the medical image by the first chest vessel segmentation model. This vessel segmentation result may be the result after distinguishing the chest vessel region image from the background image.

In this embodiment, the chest vessel region may also exist in the form of multiple labels. That is, other vascular tissues other than the aortic arch tissue (generally the common carotid artery, subclavian artery, etc.) are defined as label 1, and the aortic arch tissue is defined as label 2.

At step S703, the chest sub-medical image may be cropped by using the primary vessel segmentation result, and the cropped image is input into a second chest vessel segmentation model to obtain the vessel segmentation result of the chest sub-medical image.

Specifically, before the medical image is input into the preset second chest vessel segmentation model, the computer device performs the preprocessing on this medical image. The preprocessing may include resampling this medical image to acquire a medical image with an eleventh voxel interval, setting the window width and window level to shrink the gray value range of the medical image, and normalizing the maximum and minimum values of the image to [−1, 1] to obtain a standardized image. A second chest vessel segmentation result may be obtained by performing a feature extraction and feature mapping on the medical image by the second chest vessel segmentation model. This vessel segmentation result may be the result after distinguishing the chest vessel region image from the background image.

In this embodiment, the chest vessel region may also exist in the form of multiple labels. That is, other vascular tissues other than the aortic arch tissue (generally the common carotid artery, subclavian artery, etc.) are defined as label 1, and the aortic arch tissue is defined as label 2.

Figure 8:
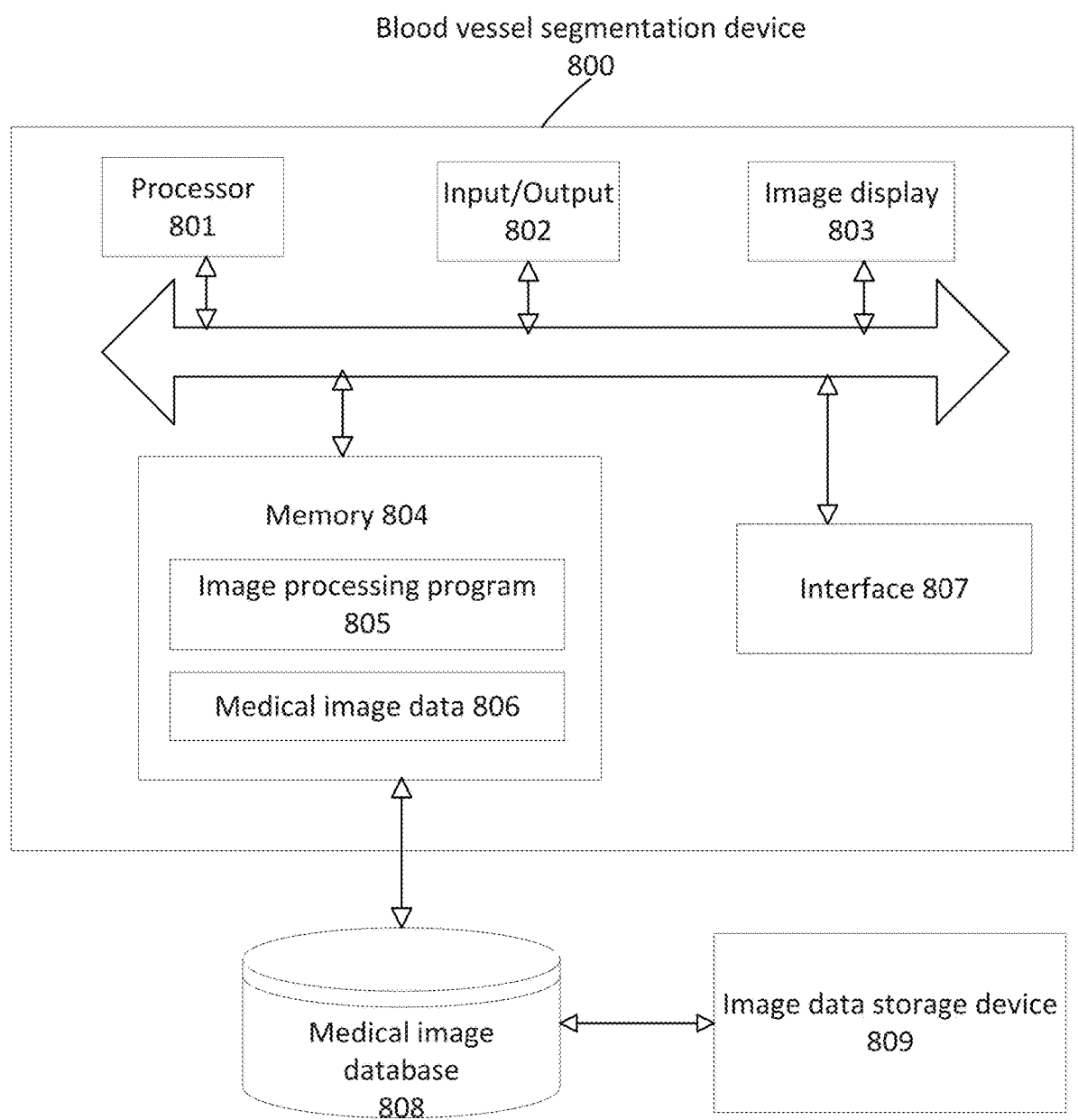
FIG. 8 shows a block diagram of a device for performing vessel segmentation in a medical image according to an embodiment of the present disclosure.

FIG. 8 shows a block diagram of a device for performing vessel segmentation in a medical image according to an embodiment of the present disclosure. As shown in FIG. 8, a vessel segmentation device 800 includes an interface 807 and a processor 801. The interface 807 may be configured for receiving a medical image for vessel segmentation containing single part or multiple parts, each of which contains different structural attributes. The processor 801 may be configured for executing the method for performing vessel segmentation in a medical image according to various embodiments of the present disclosure.

Through the interface 807, the device for performing vessel segmentation in a medical image may be connected to a network (not shown), for example but not limited to a local area network in a hospital or the Internet. However, the communication mode implemented by the interface 807 is not limited to the network, and may include NFC, Bluetooth, WIFI, etc.; it may be a wired connection or a wireless connection. Taking the network as an example, the interface 807 may connect the device for performing vessel segmentation in a medical image with external devices such as an image acquisition device (not shown), a medical image database 808 and an image data storage device 809. The image acquisition device may be any type of imaging modality, for example but not limited to computer tomography (CT), digital subtraction angiography (DSA), magnetic resonance imaging (MRI), functional MRI, dynamic contrast enhancement-MRI, diffusion MRI, spiral CT, cone beam computed tomography (CBCT), positron emission tomography (PET), single photon emission computed tomography (SPECT), X-ray imaging, optical tomography, fluorescence imaging, ultrasound imaging, radiotherapy field imaging.

In some embodiments, the vessel segmentation device 800 may be a special intelligent device or a general intelligent device. For example, the vessel segmentation device 800 may be a computer customized for image data acquisition and image data processing tasks, or a server provided in a cloud. For example, the device 800 may be integrated into the image acquisition device.

The vessel segmentation device 800 may include the processor 801 and a memory 804, and may additionally include at least one of an input/output 802 and an image display 803.

The processor 801 may be a processing device that includes one or more general processing devices, such as a micro-processor, a central processing unit (CPU) and a graphics processing unit (GPU), etc. More specifically, the processor 801 may be a complex instruction set computing (CISC) micro-processor, a reduced instruction set computing (RISC) micro-processor, a very long instruction word (VLIW) micro-processor, a processor that runs other instruction sets or a processor that runs a combination of instruction sets. The processor 801 may also be one or more dedicated processing devices, such as dedicated Integrated circuit (ASIC), field programmable gate array (FPGA), digital signal processor (DSP) and system on chip (SoC). As those skilled in the art will understand, in some embodiments, the processor 801 may be a dedicated processor instead of a general-purpose processor. The processor 801 may include one or more known processing devices, such as any of microprocessors of Pentium™, Core™, Xeon™ or Itanium™ series manufactured by Intel™, microprocessors of Turion™, Athlon™, Sempron™, Opteron™, FX™, Phenom™ series manufactured by AMD™, or microprocessors manufactured by Sun Microsystems. The processor 801 may further include graphics processing units, such as GPU from GeForce®, Quadro®, and Tesla® series manufactured by Nvidia™, and GPU of GMA, Iris™ series manufactured by Intel™, or GPU of Radeon™ series manufactured by AMD™. The processor 801 may further include accelerated processing units, such as desktop A-4 (6, 6) series manufactured by AMD™ and Xeon Phi™ series manufactured by Intel™. The disclosed embodiments are not limited to any type of processor or processor circuit, which are configured in other ways to acquiring a medical image for vessel segmentation containing multiple parts, each of which contains vessels with different structural attributes; dividing the medical image into sub-medical images according to the parts; determining individual vessel segmentation result for each part by means of using the vessel segmentation model corresponding to the part based on the sub-medical image of the part; and obtaining a vessel segmentation result of the medical image by means of fusing the individual vessel segmentation results of the sub-medical images of the parts, or manipulating any other type of data consistent with the disclosed embodiment. In addition, the term "processor" or "image processor" may include one or more processors, for example, a multi-core design or a plurality of processors, each of which has a multi-core design. The processor 801 may execute a sequence of computer program instructions stored in the memory 804 to execute various operations, processes, methods disclosed by this document.

The processor 801 may be communicatively coupled to the memory 804 and configured to perform computer-executable instructions stored therein. The memory 804 may include read-only memory (ROM), flash memory, random access memory (RAM), such as synchronous DRAM (SDRAM) or Rambus DRAM dynamic random access memory (DRAM), static memory (e.g., flash memory, static random access memory), etc., on which computer-executable instructions are stored in any format. In some embodiments, the memory 804 may store computer-executable instructions of one or more image processing programs 805. The computer program instructions may be accessed by the processor 801, read from ROM or any other suitable storage location, and loaded into the RAM for execution by the processor 801. For example, the memory 804 may store one or more of software application programs. The software application programs stored in the memory 804 may include, for example, an operating system (not shown) for a general-purpose computer system and an operating system for a soft control device.

In addition, the memory 804 may store the entire software application program or only a part of the software application program that may be executed by the processor 801 (for example, the image processing program 805). In addition, the memory 804 may store multiple software modules for implementing the process of the steps of the method for performing vessel segmentation in a medical image according to the present disclosure or the process of training the slice classification model, the corresponding vessel segmentation models of the individual parts.

In addition, the memory 804 may store data generated/cached during computer program execution, for example, medical image data 806, including medical images sent from the image acquisition device, the medical image database 808, the image data storage device 809, etc. In some embodiments, the medical image data 806 may include the medical image containing multiple parts to be segmented, and the image processing program 805 will realize the dividing of the parts, the vessel segmentation of each part and the fusion of the vessel segmentation results.

In some embodiments, the image data storage device 809 may be provided to exchange image data with the medical image database 808. The memory 804 may communicate with the medical image database 808 to obtain a medical image for vessel segmentation containing multiple parts. For example, the image data storage device 809 may reside in other medical image acquisition devices (for example, a CT scanning the patient). The patient's medical image may be transferred and saved to the medical image database 808. And the vessel segmentation device 800 may obtain the medical image of a specific patient from the medical image database 808 and perform vessel segmentation for the medical image of this specific patient.

In some embodiments, the memory 804 may communicate with the medical image database 808, so that the extracted geometric features together with the obtained vessel segmentation result of the medical image are transmitted and saved in the medical image database 808.

In addition, parameters of the trained slice classification model and/or corresponding vessel segmentation models of the individual parts may be stored in the medical image database 808 for access, acquisition and utilization by other vessel segmentation devices as needed. In this way, when confronted with patients, the processor 801 may obtain the trained slice classification model of the corresponding population and/or the vessel segmentation models of the individual parts, in order to perform vessel segmentation based on the obtained trained models.

In some embodiments, the slice classification model and/or the corresponding vessel segmentation model (especially the learning network) of the individual parts may be stored in the memory 804. Optionally, the learning network may be stored in a remote device, a database (such as the medical image database 808), a distributed device, and may be used by the image processing program 805.

In addition to displaying the medical image, the image display 803 may also display other information, such as the corresponding vessel segmentation result determined through the corresponding vessel segmentation model of the individual part, and the vessel segmentation result of the medical image after fusing the vessel segmentation results of the sub-medical images of the individual parts. For example, the image display 803 may be an LCD, CRT or LED display.

The input/output 802 may be configured to allow the vessel segmentation device 800 to receive and/or send data. The input/output 802 may include one or more digital and/or analog communication devices that allow the device 800 to communicate with users or other machines and devices. For example, the input/output 802 may include a keyboard and mouse that allows the user to provide the input.

In some embodiments, the image display 803 may present a user interface, so that the user may use the input/output 802 together with the user interface to conveniently and intuitively correct (such as edit, move, modify, etc.) the generated anatomical label.

The interface 807 may include network adaptors, cable connectors, serial connectors, USB connectors, parallel connectors, high-speed data transfer adaptors such as optical fibers, USB 6.0, lightning, wireless network adaptors such as wiki adaptors, Telecommunication (6G, 4G/LTE, etc.) adaptors. The device may connect to the network through the interface 807. The network may provide functions of local area network (LAN), wireless network, cloud computing environment (e.g., software as a service, platform as a service, infrastructure as a service, etc.), client server, wide area network (WAN), etc.

Various operations or functions are described herein, which may be implemented as software code or instructions or defined as software code or instructions. Such content may be source code or differential code ("delta" or "patch" code) that can be executed directly ("object" or "executable" form). The software code or instructions may be stored in computer readable storage medium, and when executed, may cause a machine to perform the described functions or operations and include any mechanism for storing information in the form accessible by a machine (e.g., computing device, electronic system, etc.), such as recordable or non-recordable media (e.g., read-only memory (ROM), random access memory (RAM), disk storage media, optical storage media, flash memory devices, etc.).

The foregoing description has been presented for illustrative purposes. It is not exhaustive, and is not limited to the precise form or embodiment disclosed. In view of the specification and practice of the disclosed embodiment, modifications and adaptations of the embodiment will be obvious.

Exemplary Methods described herein may be machine or computer-implemented at least in part. Some examples may include a computer-readable medium or machine-readable medium encoded with instructions operable to configure an electronic device to perform methods as described in the above examples. An implementation of such methods may include software code, such as microcode, assembly language code, a higher-level language code, or the like. The various programs or program modules may be created using a variety of software programming techniques. For example, program sections or program modules can be designed in or by means of Java, Python, C, C++, assembly language, or any known programming languages. One or more of such software sections or modules can be integrated into a computer system and/or computer-readable media. Such software code can include computer readable instructions for performing various methods. The software code may form portions of computer program products or computer program modules. Further, in an example, the software code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. It is intended, therefore, that the descriptions and examples be considered as examples only, with a true scope and spirit being indicated by the following claims and their full scope of equivalents.

The above description is intended to be illustrative, and not restrictive. For example, the above-described examples (or one or more aspects thereof) may be used in combination with each other. Other embodiments can be used by one of ordinary skill in the art upon reviewing the above description. Also, in the above Detailed Description, various features may be grouped together to streamline the disclosure. This should not be interpreted as intending that an unclaimed disclosed feature is essential to any claim. Rather, inventive subject matter may lie in less than all features of a disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method for performing vessel segmentation in a medical image, comprising:
   receiving the medical image containing multiple parts, which respectively contain vessels with different structural attributes;
   dividing, by a processor, the medical image into sub-medical images according to the multiple parts, wherein the medical image is a 3D medical image and each sub-medical image of the sub-medical images is identified as a slice of interest at an adjoining portion of adjacent parts among the multiple parts in the 3D medical image by using a slice classification model;
   determining, by the processor, an individual vessel segmentation result for each of the multiple parts by applying a respective vessel segmentation model of a plurality of vessel segmentation modes to a corresponding sub-medical image of the sub-medical images;
   selecting, by the processor, at least one part from the multiple parts to be a part prone to interruption in the individual vessel segmentation result of a vessel at an adjoining portion of adjacent parts of the multiple parts; and
   obtaining, by the processor, a vessel segmentation result of the medical image by fusing individual vessel segmentation results of the sub-medical images of the multiple parts based on the at least one part selected to be the part prone to interruption in the vessel segmentation result of the vessel at the adjoining portion of the adjacent parts.

2. The method according to claim 1, wherein the structural attributes of the vessels comprise at least one of a morphology or a size.

3. The method according to claim 1, wherein the slice classification model is a two-dimensional learning network trained using training samples with classification information of a slice of a corresponding part.

4. The method according to claim 1, wherein the method further comprising: performing a standardized processing on the medical image or the sub-medical images before further processing on the medical image or the sub-medical images by the processor.

5. The method according to claim 4, wherein the standardized processing comprises:
   resampling the medical image or the sub-medical images to a preset voxel interval; and
   normalizing grayscale values of the resampled medical image or the sub-medical images to a preset grayscale value range.

6. The method according to claim 1, wherein the vessel segmentation model that corresponds to the one of the multiple parts is trained separately using training samples with classification information of a vessel of a corresponding part.

7. The method according to claim 6, wherein the classification information of the vessel of the corresponding part comprises multiple labels.

8. The method according to claim 1, wherein determining, by the processor, the individual vessel segmentation result for each of the multiple parts by applying the respective vessel segmentation model of the plurality of vessel segmentation modes to the corresponding sub-medical image of the sub-medical images comprises:
   performing a coarse segmentation in the sub-medical images of each of the multiple parts to obtain a first image patch containing a target region of the vessel to be segmented; and
   applying a first vessel segmentation model to the first image patch containing the target region, to obtain a first vessel segmentation result of the corresponding sub-medical image of the part.

9. The method according to claim 8, further comprising:
   extracting a centerline from the first vessel segmentation result of at least one part;
   cropping a second image patch at an end of the extracted centerline;
   applying a second vessel segmentation model to the second image patch at the end, to obtain a second vessel segmentation result of the end; and
   fusing the first vessel segmentation result and the second vessel segmentation result, to obtain the individual vessel segmentation result of the corresponding sub-medical image.

10. The method according to claim 9, wherein the at least one part includes the multiple parts, or a part of interest preset by a doctor in the multiple parts.

11. The method according to claim 9, wherein the at least one part from the multiple parts selected to be the part prone to interruption in the individual vessel segmentation result of the vessel at the adjoining portion of adjacent parts of the medical image satisfies at least one of the following conditions:
   a diameter of the vessel at the end of the adjoining portion is less than a first predetermined threshold;
   a curvature of the vessel at the end of the adjoining portion is larger than a second predetermined threshold; or
   a contrast of the vessel at the end of the adjoining portion to a surrounding region is less than a third predetermined threshold.

12. The method according to claim 1, wherein the multiple parts include at least one of different body parts, different organs, or different organ parts in a same organ.

13. The method according to claim 1, wherein the medical image comprises at least one of a head and neck CTA image, a head and neck MRA image, or a lung CT image.

14. The method according to claim 13, wherein the medical image is the head and neck CTA image or the head and neck MRA image, and the multiple parts comprise head, neck and chest,
   wherein determining the individual vessel segmentation result for each of the multiple parts by applying the respective vessel segmentation model of the plurality of vessel segmentation modes to the corresponding sub-medical image of the sub-medical images comprises:

segmenting a skull of a head sub-medical image through a preset threshold range of bone tissue grayscale, cropping the head sub-medical image containing a skull region, and applying a first head vessel segmentation model to the cropped head sub-medical image, to obtain a primary vessel segmentation result;

extracting a centerline from the primary vessel segmentation result, cropping an image patch at an end of the extracted centerline, and applying a second head vessel segmentation model to the cropped image patch, to obtain a head vessel segmentation result of the end; and fusing the primary vessel segmentation result and the head vessel segmentation result of the end, to obtain the individual vessel segmentation result of the head sub-medical image.

15. The method according to claim 13, wherein determining the individual vessel segmentation result for each of the multiple parts by applying the respective vessel segmentation model of the plurality of vessel segmentation modes to the corresponding sub-medical image of the sub-medical images comprises:

applying a first neck vessel segmentation model to a neck sub-medical image, to obtain a primary vessel segmentation result;

cropping the neck sub-medical image by using the primary vessel segmentation result and applying a second neck vessel segmentation model to the cropped neck sub-medical image, to obtain a refined vessel segmentation result;

extracting a centerline from the refined vessel segmentation result, cropping an image patch at an end of the extracted centerline, and applying a third neck vessel segmentation model to the cropped image patch, to obtain a neck vessel segmentation result of the end; and fusing the primary vessel segmentation result and the neck vessel segmentation result of the end, to obtain the individual vessel segmentation result of the neck sub-medical image.

16. The method according to claim 13, wherein determining the individual vessel segmentation result for each of the multiple parts by applying the respective vessel segmentation model of the plurality of vessel segmentation modes to the corresponding sub-medical image of the sub-medical images comprises:

applying a first chest vessel segmentation model to a chest sub-medical image to obtain a primary vessel segmentation result, cropping the chest sub-medical image by using the primary vessel segmentation result and applying a second chest vessel segmentation model to the cropped chest sub-medical image to obtain the individual vessel segmentation result of the chest sub-medical image.

17. A device for performing vessel segmentation in a medical image, comprising:

an interface, configured to receive the medical image containing multiple parts, which respectively contain vessels with different structural attributes; and a processor, configured to:

divide the medical image into sub-medical images according to the multiple parts;

determine an individual vessel segmentation result for each of the multiple parts by applying a respective vessel segmentation model of a plurality of vessel segmentation modes to a corresponding sub-medical image of the sub-medical images;

select at least one part from the multiple parts to be a part prone to interruption in the individual vessel segmentation result of a vessel at an adjoining portion of adjacent parts of the medical image; and obtain a vessel segmentation result of the medical image by fusing individual vessel segmentation results of the sub-medical images of the multiple parts based on the at least one part selected to be the part prone to interruption in the vessel segmentation result of the vessel at the adjoining portion of the adjacent parts.

18. The device according to claim 17, wherein structural attributes of the vessel comprise at least one of a morphology or a size.

19. A non-transitory computer readable medium having instructions stored thereon, wherein the instructions, when executed by a processor, implements a method for performing vessel segmentation in a medical image containing multiple parts, comprising:

dividing the medical image into sub-medical images according to the multiple parts;

determining an individual vessel segmentation result for each of the multiple parts by applying a respective vessel segmentation model of a plurality of vessel segmentation modes to a corresponding sub-medical image of the sub-medical images;

select at least one part from the multiple parts to be a part prone to interruption in the individual vessel segmentation result of a vessel at an adjoining portion of adjacent parts of the medical image; and obtaining a vessel segmentation result of the medical image by fusing individual vessel segmentation results of the sub-medical images of the parts based on the at least one part selected to be the part prone to interruption in the vessel segmentation result of the vessel at the adjoining portion of the adjacent parts.

20. The non-transitory computer readable medium according to claim 19, wherein the at least one part from the multiple parts selected to be the part prone to interruption in the individual vessel segmentation result of the vessel at the adjoining portion of adjacent parts of the medical image satisfies at least one of the following conditions:

a diameter of the vessel at an end of the adjoining portion is less than a first predetermined threshold;

a curvature of the vessel at the end of the adjoining portion is larger than a second predetermined threshold; or a contrast of the vessel at the end of the adjoining portion to a surrounding region is less than a third predetermined threshold.

* * * * *